United States Patent
Soro et al.

(10) Patent No.: US 10,743,312 B2
(45) Date of Patent: Aug. 11, 2020

(54) SYSTEMS AND METHODS FOR MEDICAL BODY AREA NETWORK FREQUENCY BAND SWITCHING

(71) Applicant: General Electric Company, Schenectady, NY (US)

(72) Inventors: Stanislava Soro, Niskayuna, NY (US); S M Hasan, Rexford, NY (US); Matthew Pekarske, Milwaukee, WI (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 15/975,432

(22) Filed: May 9, 2018

(65) Prior Publication Data

US 2019/0349929 A1 Nov. 14, 2019

(51) Int. Cl.
| | |
|---|---|
| H04W 4/02 | (2018.01) |
| H04W 72/04 | (2009.01) |
| A61B 5/00 | (2006.01) |
| H04W 28/26 | (2009.01) |
| H04L 29/08 | (2006.01) |
| H04W 84/18 | (2009.01) |

(52) U.S. Cl.
CPC ....... *H04W 72/0453* (2013.01); *A61B 5/0024* (2013.01); *H04L 67/125* (2013.01); *H04W 28/26* (2013.01); *H04W 84/18* (2013.01)

(58) Field of Classification Search
CPC ... H04L 1/0021; H04L 43/0829; H04L 12/26; H04L 67/12; H04W 4/008; H04W 4/023; H04W 72/0453; H04W 28/26; H04B 7/088; H04B 7/318; H04B 7/0619; A61B 5/0024

See application file for complete search history.

(56) References Cited

U.S. PATENT DOCUMENTS

| | | | | |
|---|---|---|---|---|
| 9,041,532 B1* | 5/2015 | Hasan | ............ | A61B 5/002 340/10.1 |
| 9,307,343 B2* | 4/2016 | Lim | ............ | H04W 4/70 |
| 9,603,024 B2* | 3/2017 | Wang | ............ | H04W 16/14 |
| 9,943,229 B1* | 4/2018 | Wik | ............ | A61B 5/0024 |
| 10,230,491 B2* | 3/2019 | Soro | ............ | H04L 1/0002 |
| 10,306,407 B2* | 5/2019 | Soro | ............ | H04W 4/023 |
| 2008/0228045 A1 | 9/2008 | Gao et al. | | |
| 2011/0149759 A1 | 6/2011 | Jollota | | |

(Continued)

*Primary Examiner* — Hahn N Nguyen

(74) *Attorney, Agent, or Firm* — Hanley, Flight and Zimmerman, LLC

(57) ABSTRACT

Apparatus, systems and articles of manufacture to provide improved, dynamic medical body area network communication among available frequency bands in a healthcare environment are disclosed and described. An example apparatus includes at least one processor to determine, based on a plurality of control messages indicating availability of a second frequency spectrum and timing of receipt of the plurality of control messages, a first mode or a second mode for medical body area network (MBAN) communication, the first mode specifying MBAN communication in a first frequency spectrum and the second mode specifying MBAN communication in the first frequency spectrum and the second frequency spectrum. The example apparatus includes at least one communication interface to receive the control messages and transmit an indication of a missed control message.

17 Claims, 11 Drawing Sheets

(56) References Cited

U.S. PATENT DOCUMENTS

| | | |
|---|---|---|
| 2013/0023215 A1 | 1/2013 | Wang |
| 2013/0245387 A1 | 9/2013 | Patel |
| 2014/0036863 A1 | 2/2014 | Lim et al. |
| 2014/0148100 A1 | 5/2014 | Kim et al. |
| 2015/0238082 A1 | 8/2015 | Soro et al. |
| 2016/0013872 A1 | 1/2016 | Astrand et al. |
| 2016/0066788 A1 | 3/2016 | Tran et al. |
| 2016/0135206 A1 | 5/2016 | Wang |
| 2016/0135685 A1 | 5/2016 | Cao |
| 2017/0111824 A1 | 4/2017 | Wang |
| 2017/0170924 A1 | 6/2017 | Soro et al. |

\* cited by examiner

SYSTEMS AND METHODS FOR MEDICAL BODY AREA NETWORK FREQUENCY BAND SWITCHING

FIELD OF THE DISCLOSURE

This disclosure relates generally to medical body area networks, and, more particularly, to frequency band switching for medical body area networks.

BACKGROUND

In wireless patient monitoring, device(s) on a patient use, by default, frequencies within a pre-defined spectrum (e.g., an industrial, scientific and medical (ISM) radio band such as 2.4-2.4835 GHz, etc.) for transmitting and receiving patient sensor data. While operating in a healthcare facility, such as a hospital, etc., these devices have access to a protected frequency spectrum known as a medical body area network (MBAN, such as 2360-2400 MHz, etc.). MBAN spectrum is split into two sub-bands (2360-2390 MHz and 2390-2400 MHz) and, for the purposes of this disclosure, the following differences are highlighted. The 2360-2390 MHz spectrum is subject to Frequency Coordination per FCC Part 95.2509 and use of this spectrum is restricted to indoors only. The 2390-2400 MHz frequency band does not require Frequency Coordination and does not have restrictions on whether it can operate indoors or outdoors. For example, within the healthcare facility, an MBAN device can be authorized for access to the MBAN spectrum (2.36-2.39 GHz) from a third-party Frequency Coordinator regulated by the Federal Communications Commission (FCC). However, once the device leaves the healthcare facility, access to the pre-defined, reserved, or "protected" MBAN communication spectrum is denied.

A body area network is a wireless network of wearable computing devices. An MBAN is a wireless network of wearable computing devices that monitor and/or affect patient health, such as sensors, pumps, meters, monitors, etc. An MBAN is a low power network including a plurality of body-worn sensors that transmit a variety of patient data (e.g., temperature, blood glucose level, blood pressure, pulse and respiratory function, etc.) to a control device. The MBAN eliminates cables tethering the patient to a bed and provides real-time (or substantially real time given data transmission and processing latency) data to healthcare practitioners. Wireless medical devices can be used to actively monitor a patient's health, including blood glucose and pressure monitoring, delivery of electrocardiogram readings, neonatal monitoring, etc. Data can be gathered for storage, processing, transmission, etc., such as to a control device, patient electronic medical record, display, etc. Connected device(s) can also be used to deliver medical therapy to certain body area(s), for example.

BRIEF DESCRIPTION OF THE DRAWINGS

The features and technical aspects of the system and method disclosed herein will become apparent in the following Detailed Description set forth below when taken in conjunction with the drawings in which like reference numerals indicate identical or functionally similar elements.

BRIEF DESCRIPTION

Figure 1A:
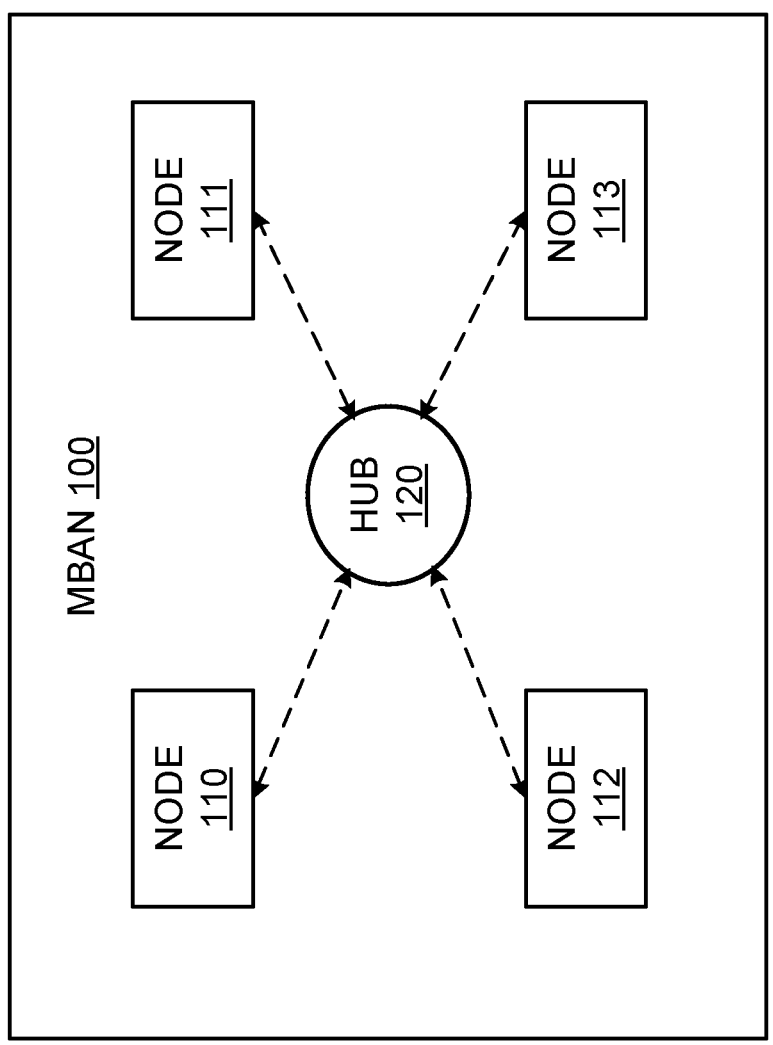
FIG. 1A illustrates an example medical body area network (MBAN) including a plurality of nodes or devices in communication with a hub.

Certain examples disclosed herein facilitate improved, dynamic medical body area network communication among available frequency bands in a healthcare environment.

An example apparatus includes at least one processor to determine, based on a plurality of control messages indicating availability of a second frequency spectrum and timing of receipt of the plurality of control messages, a first mode or a second mode for medical body area network (MBAN) communication, the first mode specifying MBAN communication in a first frequency spectrum and the second mode specifying MBAN communication in the first frequency spectrum and the second frequency spectrum. The example apparatus includes at least one communication interface to receive the control messages and transmit an indication of a missed control message.

Certain examples provide at least one computer-readable storage medium including instructions. The example instructions, when executed, cause at least one processor to at least determine, based on a plurality of control messages indicating availability of a second frequency spectrum and timing of receipt of the plurality of control messages, a first mode or a second mode for medical body area network (MBAN) communication, the first mode specifying MBAN communication in a first frequency spectrum and the second mode specifying MBAN communication in the first frequency spectrum and the second frequency spectrum. The example instructions, when executed, cause the at least one processor to transmit an indication of a missed control message.

Certain examples provide a method including determining, using at least one processor based on a plurality of control messages indicating availability of a second frequency spectrum and timing of receipt of the plurality of control messages, a first mode or a second mode for medical body area network (MBAN) communication, the first mode specifying MBAN communication in a first frequency spectrum and the second mode specifying MBAN communication in the first frequency spectrum and the second frequency spectrum. The example method also includes transmitting, using the at least one processor, an indication of a missed control message.

DETAILED DESCRIPTION

In the following detailed description, reference is made to the accompanying drawings that form a part hereof, and in which is shown by way of illustration specific examples that may be practiced. These examples are described in sufficient detail to enable one skilled in the art to practice the subject matter, and it is to be understood that other examples may be utilized and that logical, mechanical, electrical and other changes may be made without departing from the scope of the subject matter of this disclosure. The following detailed description is, therefore, provided to describe an exemplary implementation and not to be taken as limiting on the scope of the subject matter described in this disclosure. Certain features from different aspects of the following description may be combined to form yet new aspects of the subject matter discussed below.

When introducing elements of various embodiments of the present disclosure, the articles "a," "an," "the," and "said" are intended to mean that there are one or more of the elements. The terms "comprising," "including," and "having" are intended to be inclusive and mean that there may be additional elements other than the listed elements.

As used herein, the terms "system," "unit," "module," "engine," etc., may include a hardware and/or software system that operates to perform one or more functions. For example, a module, unit, or system may include a computer processor, controller, and/or other logic-based device that performs operations based on instructions stored on a tangible and non-transitory computer readable storage medium, such as a computer memory. Alternatively, a module, unit, engine, or system may include a hard-wired device that performs operations based on hard-wired logic of the device. Various modules, units, engines, and/or systems shown in the attached figures may represent the hardware that operates based on software or hardwired instructions, the software that directs hardware to perform the operations, or a combination thereof.

Example Medical Body Area Network Systems

Certain examples of the presently disclosed technology improve frequency switching among allowed bands for medical data communication with medical body area networks (MBANs). Certain examples improve reliability and efficiency of data delivery by balancing medical and non-medical devices among available frequency spectra in a healthcare environment such as a hospital, clinic, surgical center, doctor's office, etc.

Certain examples disclose and describe systems and methods for switching communications of an MBAN between the industrial, scientific and medical (ISM) (e.g., 2.4-2.4835 GHz) and MBAN (e.g., 2.36-2.4 GHz) frequency bands. MBAN devices can operate in the ISM spectrum, which is often shared with other medical and non-medical devices. To improve the reliability of data delivery, MBAN devices can operate in the MBAN portion of the frequency spectrum on a secondary basis. That is, MBAN devices are to obtain approval from a primary user of the MBAN spectrum in order to (conditionally) use the increased MBAN frequency band. For example, while operating in a healthcare facility, such as a hospital, clinic, doctor's office, pharmacy, etc., MBAN devices have access to the protected frequency spectrum of the MBAN (2.36-2.39 GHz) pending permission from the primary user, frequency coordinator, etc. An MBAN device is to evacuate the MBAN spectrum when the MBAN spectrum is requested back by the primary user and/or when the MBAN device stops receiving control messages (e.g., from a frequency coordinator, etc.) which carry information regarding the MBAN spectrum usage.

Certain examples provide a patient monitoring system and associated method(s) with periodic control message dissemination throughout a healthcare environment (e.g., hospital, clinic, doctor's office, etc.). Certain examples define a message structure, enabled system features, and multifrequency protocol with retransmissions including frequency band switching support.

An MBAN is a wireless patient monitoring network that includes a) one or more physiological sensors attached to a patient to capture patient data and b) a hub (e.g., on patient or off patient), also referred to as a programmer/control device, which collects the patient data and acts as a network master. Most MBAN devices operate in the ISM band (2.4-2.4835 GHz), which is commonly shared with many other wireless devices. As discussed above, since many devices simultaneously operate in the same frequency band, many issues, such as high signal interference, spectrum congestion and packet loss, etc., can occur, causing the degradation of wireless links and loss of patient's physiological data, for example. One way to overcome this problem is to provide additional spectrum for MBAN devices to operate. The MBAN frequency band (e.g., 2.36-2.4 GHz) in the USA can be used by medical devices for transmission of medical (e.g., non-voice) patients' data. The MBANs can operate on a secondary basis in a lower portion of this band (e.g., from 2360-2390 MHz). Operating on a secondary basis indicates that their operations in this portion of the band are subject to approval by a primary band user. In the US, the Federal Communications Commission (FCC) regulates operations of MBANs in this band through an entity referred to as an MBAN coordinator or MBAN frequency coordinator, which is a body outside of the hospital or other healthcare environment that informs the hospital about the availability of MBAN channels for use by the MBAN devices inside the hospital, for example.

FIG. 1A illustrates an example MBAN 100 including a plurality of nodes or devices 110-113 in communication with a hub 120 (also referred to as an MBAN programmer/controller (P/C) device). The hub device 120 can be a master programmer/control transmitter included in a device close to the patient. The nodes 110-113 are client transmitters (e.g., body sensors and/or other medical/monitoring devices) worn by the patient and transmit information to the hub 120 when in communication with the hub 120. The hub 120 transmits data messages to the nodes 110-113 to specify, for example, a transmit frequency to be used for data communication.

For example, 40 MHz of MBAN spectrum (e.g., from 2360-2400 MHz or 2.36-2.4 GHz, etc.) can be allocated for MBAN communication. The 2360-2390 MHz portion of the band (a secondary or lower portion of the MBAN spectrum) is reserved for indoor use inside healthcare facilities (e.g., with a transmit power of 1 mW measured over 1 MHz bandwidth, etc.) and involves registration with an MBAN frequency coordinator for use. The 2390-2400 MHz band (a primary or upper portion of the MBAN spectrum) does not involve registration and coordination and can be used in any location (e.g., indoor or outdoor, with a transmit power of 20 mW measured over 5 MHz bandwidth, etc.).

Since many devices, medical and otherwise, operate in the 2.4 GHz ISM band, this ISM band (2.4-2.4835 GHz) can become quite crowded, resulting in device interference, data loss, etc. Enabling an MBAN device to utilize the lower spectrum (e.g., 2.36-2.4 GHz) as much as possible while within a healthcare facility helps to ease conflicts in the 2.4 GHz ISM frequency band and facilitate improved, more accurate, and faster communications between MBANs and hospital networks.

The hub 120 aggregates patient data from the node devices 110-113 under its control and transmits that information (e.g., via a network, such as a local area network (LAN) and/or other Ethernet, WiFi, Bluetooth, etc., network associated with the healthcare facility) to a control point and/or other data storage and/or processing server to monitor and process the collected patient data. For example, the monitored data can be used to trigger an alert for the patient and/or a healthcare practitioner, adjust a treatment plan, schedule an appointment, etc., and/or other clinical task.

In certain examples, the control point for the healthcare facility coordinates operations for the MBAN 100 (and other MBANs that may be in the healthcare facility). The control point helps to coordinate MBAN operations in the 2360-2390 MHz frequency band and protect MBAN communications from interference within that protected/reserved band. The control point also restricts MBAN communication when such communication may interfere with communication from "primary" devices or users in a healthcare environment (e.g., hospital systems, healthcare providers, aeronautical mobile telemetry, etc.). In certain examples, the control point receives an electronic key specifying frequency(-ies) for use by the MBAN 100 and its devices. The control point sends a control message to the hub 120 to specify authorized frequency(-ies) and/or other operating parameter(s) for the hub 120 and nodes 110-113 in that MBAN 100.

Certain examples provide systems and associated methods to provide automatic frequency band selection for wireless patient monitoring devices depending on their physical location (e.g., either inside or outside of a healthcare facility, etc.). Certain examples provide automated and/or other seamless frequency band selection based on multiple factors. Example factors for automated frequency band selection include location, active band monitoring, coordination, etc.

For example, location can influence frequency selection. If the MBAN 100 is within the healthcare facility (e.g., in the hospital, etc.), then devices in the MBAN 100 can use the ISM plus full MBAN frequency range (e.g., full MBAN range of 2.36-2.4 GHz with reduced outdoor range of 2.39-2.4 GHz). However, outside the bounds of the healthcare facility, devices of the MBAN 100 are limited to the ISM plus a reduced MBAN frequency range.

Another example factor is active band monitoring. For example, access to the MBAN 100 can be based on the detection of wireless implants using a frequency band. The wireless implants have priority usage of the frequency band, and MBAN 100 devices are to vacate that frequency band automatically after detecting the presence of the wireless implants. However, if no competing wireless implants are detected, MBAN 100 devices can proceed to use the frequency band.

Another example factor is coordination. For example, a Federal Communications Commission (FCC)-assigned coordinator in an area sends control messages to nearby hospitals to indicate availability of the full MBAN spectrum for in-hospital use at a time. Wireless devices defer to reduced frequency bands (ISM) as indicated by these control messages.

Thus, certain examples use these and/or other factors to provide information to medical devices, including medical body area networks (MBANs) 100, regarding location in or outside of a healthcare facility, such as a hospital, clinic, doctor's office, etc., based on which the devices are permitted or not permitted to operate in the MBAN frequency band (e.g., 2360-2390 MHz).

Figure 1B:
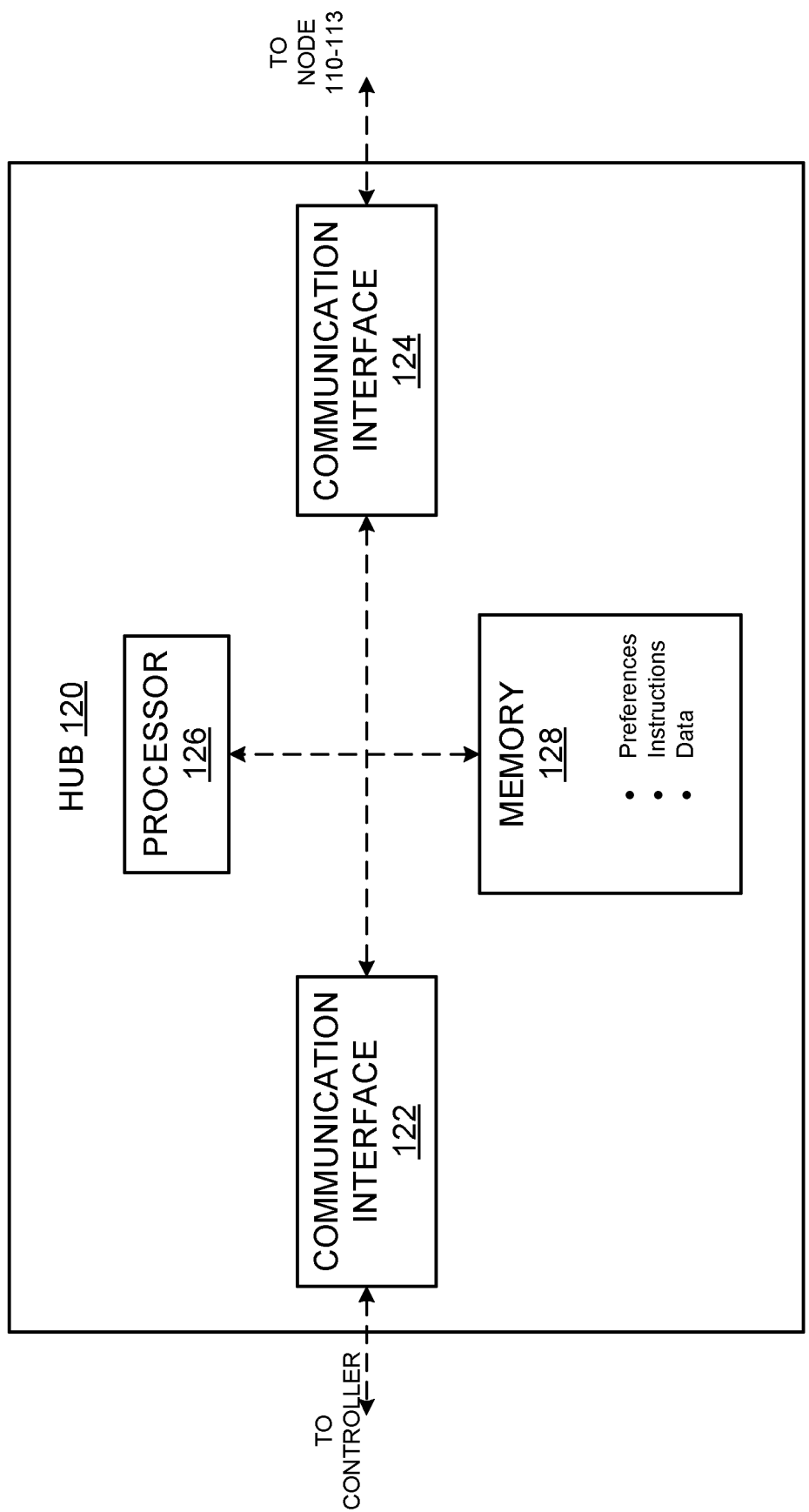
FIG. 1B illustrates an example implementation of the hub of the example MBAN of FIG. 1A

FIG. 1B depicts an example implementation of the MBAN hub device 120. As shown in the example of FIG. 1A, the hub 120 can include a first communication interface 122 to communicate with a controller such as a frequency controller, control point, hospital coordinator, and/or other computing device, etc. The hub 120 can receive frequency spectrum and/or other control information and provide feedback to the controller via the first communication interface 122, for example. The example hub 120 of FIG. 1B includes a second communication interface 124 to communicate with one or more nodes 110-113. The hub 120 can receive sensor data and/or other input from the node(s) 110-113, provide instruction to the node(s) 110-113, etc., via the second communication interface 124, for example. The example hub 120 of FIG. 1B includes a processor 126 to process received messages, instructions, data, etc., to operate the hub 120 and its communication interfaces 122, 124. The example hub 120 includes a memory 128 which can store instructions, data, preferences, etc. The processor 126 can execute instructions in the memory 128, store information from communication interfaces 122, 124 in the memory 128, store and/or update preference and/or profile information in the memory 128, etc. For example, the processor 126 can store in indication of allowed frequency band(s), a default frequency/channel, and/or other configuration information in the memory 128.

Figure 2:
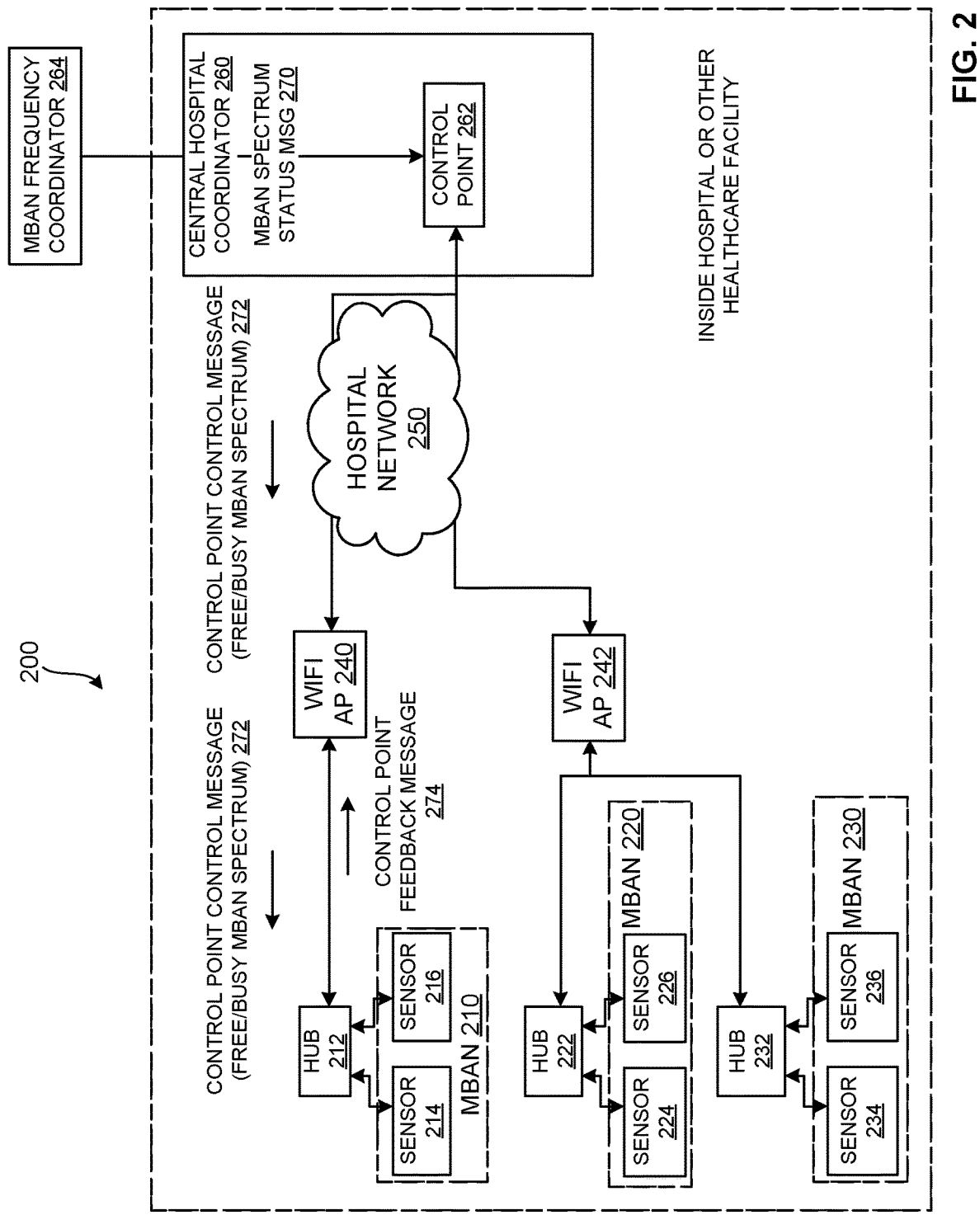
FIGS. 2-3 illustrate example communication infrastructure of a wireless patient monitoring system.

FIG. 2 illustrates an example patient monitoring system architecture 200. The example system 200 is illustrated in the context of a hospital but can be applied to other healthcare facilities or environments such as clinics, doctor's offices, etc.

The example system 200 includes a plurality of MBANs 210, 220, 230. Each MBAN 210, 220, 230 includes a hub 212, 222, 232 and associated sensors 214, 216, 224, 226, 234, 236. The hub 212 communicates with a wireless access point (AP) 240. The hubs 222, 232 communicate with a wireless AP 242. The wireless APs 240, 242 facilitate access to a hospital network 250 which interacts with a central hospital coordinator 260. The central coordinator 260 includes a control point 262 to coordinate messages and control of the MBANs 210, 220, 230 and/or other hardware/software in the system 200. In certain examples, the central hospital coordinator 260 receives input from an MBAN frequency coordinator 264 to set certain frequency(-ies) for MBAN communication usage. Thus, the MBAN frequency coordinator 264 informs the central coordinator 260 of the hospital and/or other healthcare environment regarding availability of the MBAN spectrum (2360-2390 MHz).

As shown in the example of FIG. 2, the central coordinator 260 generates a MBAN spectrum status message 270 regarding a status of a frequency spectrum available to the MBAN 210, 220, 230. The status message 270 is provided to the control point 262, hosted by the central coordinator 260, which communicates via the hospital network 250 to provide a control point control message (CPCM) 272 regarding free and/or busy MBAN spectrum (e.g., available MBAN communication frequency spectrum). The control message 272 can be routed by the APs 240, 242 to the hubs 212, 222, 232. Thus, the hubs 212, 222, 232 are made aware of available frequency spectrum for MBAN communication (or lack/restriction thereof) inside the hospital and/or other healthcare facility.

The example system 200 enables frequency band switching by the MBAN hubs 212, 222, 232. Information regarding MBAN spectrum availability is obtained from an FCC-designated body (e.g., an MBAN Frequency coordinator). This message is received by the hospital (e.g., the central coordinator 260). The central coordinator 260 includes a service point (e.g., the control point 262) that periodically broadcasts MBAN status information in a control message 272 to all MBAN hubs 212, 222, 232 (e.g., patient monitors). The control message 272 is transmitted through the existing hospital network infrastructure 240, 242, 250 (e.g., WiFi network, etc.).

An example CPCM 272 can be formatted as follows:

| Field Name | Field Size [bytes] | Value/Purpose |
| --- | --- | --- |
| mbanStatus | 1 | Enables/disables (1/0) usage of MBAN spectrum to MBAN clients |
| mbanOnly | 1 | Carries information on a portion of the spectrum in which an MBAN should operate:<br>mbanOnly = 1 – MBAN client operates in MBAN spectrum only<br>mbanOnly = 0 – MBAN client operates in MBAN and ISM spectrum |
| cpcmPeriod | 4 | Period between two CPCM messages in seconds |
| cpcmTimeWindow | 4 | Rolling time window during which the MBAN Programmer/Controller (P/C) device (e.g., hub) counts the number of received messages |
| cpcmMissed_max | 2 | Threshold of missing CPCMs during integer cpcmTimeWindow_seconds. If the number of missed CPCM messages is greater than this threshold, the P/C device (e.g., hub) will default its operations to the ISM band. |
| mbanAvailableChannelsBitmap | 4 | Channel numbers of available MBAN channel. Note that there can be multiple MBAN-AVAILABLE-CHANNEL entries, one for each available channel (in the range of [1, 20], inclusive). |

CPCMs 272 can be distributed throughout the hospital and/or other healthcare facility. There are several ways to distribute the CPCM 272 by the control point service 262. For example, the control point service 262 can periodically transmit CPCMs 272 to all MBAN hub devices 212-232 throughout the hospital network 250 (e.g., via WiFi access points 240, 242, etc.).

Alternatively or in addition, CPCMs 272 can be disseminated throughout the system using a Data Centric Publish Subscribe (DCPS) communication model. Such a publish-subscribe model can be implemented using a Data Distribution Service (DDS) specification, for example, which provides one or more standardized application programming interfaces (APIs) used to communicate data between distributed applications.

In certain examples, one or more MBAN hubs 212-232 can provide feedback to the control point service 262 through a control point feedback message 274. Thus, the MBAN hub 212-232 can provide the control point service 262 with an acknowledgement of receipt of the CPCM 272, access to spectrum/spectra, and/or other status information, etc.

Figure 3:
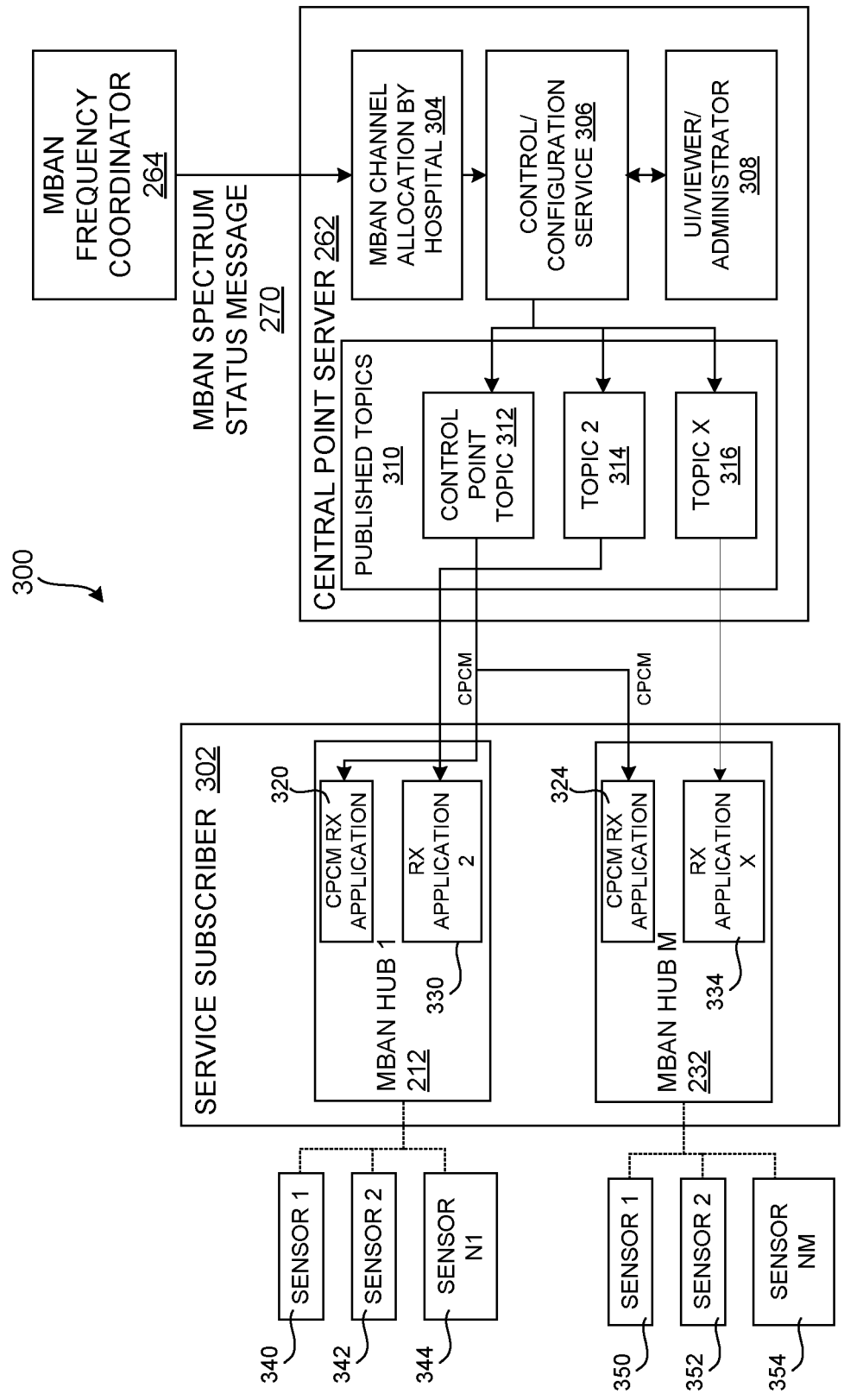

FIG. 3 illustrates an example publish-subscribe communication model 300 for CPCM 272 dissemination used to deliver the CPCM 272 to the MBAN Hub 212-232. End point nodes, which correspond to the MBAN Hubs 212-232 and central hospital coordinator 260/control point server 262, communicate by sending (e.g., publishing) and receiving (e.g., subscribing) specific data. Rather than establishing explicit connection(s) between publisher and receiver, the central point server 262 can publish various topics, where each topic provides a service-specific data. For example, the published topics can support services such as location service, over-the-air update, rescue service, etc. One of these topics can be a control point message topic, which provides the data fields of the CPCM message 272. The MBAN hub 212-232 subscribes to the control point message topic, in order to receive CPCM 272 from the publisher.

Data distribution between subscriber and publisher can be defined and controlled using various quality of service (QoS) settings. These settings can define the publishing rate (e.g., how often the publisher publish the data) and subscribing rate (e.g., how often the subscriber checks for the new data). For example, the subscribing rate can be equivalent to the CPCM period defined in the table above.

As shown in the example of FIG. 3, which illustrates a publish-subscribe model 300 for CPCM 272 dissemination, a service subscriber 302, including one or more MBAN hubs 212-232 communicates with the central point server 262 operating as a publisher for CPCMs 272. The central point server 262 receives the MBAN spectrum status message 270 via the central coordinator 260 and/or 264 to generate an MBAN channel allocation by hospital 304, which is provided to a control/configuration service 306. The channel allocation and/or other control and/or configuration information can be displayed via a user interface/viewer 308 providing administrator functions to a user (e.g., accept, reject, modify, override, provide feedback, store, report, configure, etc.).

The configuration/control service 306 generates one or more published topics 310 to be disseminated to subscribers 302 including MBAN hubs 212-232, for example. Subscribers 302 can subscribe to one or more topics 310 including an MBAN frequency or control point message topic 312. The control point topic 312 transmits CPCMs 272 to subscribing MBAN hubs 212-232, and other topics 314, 316 transmit other messages to subscribing MBAN hubs 212-232.

As shown in the example of FIG. 3, data published by the control point message topic 312 is received by a CPCM receiver (RX) application 320-324 on each MBAN hub 212-232. The data can be received by setting up a callback routine by the CPCM RX application 320-324 to receive the CPCM message 272 as the message 272 is published, or the application 320-324 can check (e.g., query) the publisher 262 periodically to receive the CPCM 272, for example. The CPCM 272 can be received in other ways as well.

Additionally, other topic(s) 314-316 can be received via another receive (RX) application 330-334 on each MBAN hub 212-232, for example.

Based on the received CPCM 272, an indication of available spectrum (e.g., MBAN only, MBAN+ISM, etc.) is provided to each subscribing MBAN hub 212-232. The hub 212-232 can then collect and transmit information from one or more connected sensors 340-354 via the available communication frequency spectrum (e.g., MBAN only, MBAN+ ISM, etc., per the CPCM 272).

In certain examples, the MBAN hub device 212-232 processes the CPCM message 272 as it is received. In order to use the MBAN spectrum, the hub device 212-232 is to continuously stay informed about the availability of the MBAN spectrum through undisturbed reception of CMCMs 272. The CPCM message 272 carries information regarding a period between two CPCM messages (cpcmPeriod) as well as a time window (cpcmTimeWindow) during which the hub 212-232 counts a number of lost consequent CPCM messages 272. If the number of counted lost messages is higher than a threshold (cpcmMissed_max), then the MBAN 210-230 is to evacuate the MBAN spectrum, since it does not have the latest information about the status of the MBAN spectrum.

If the MBAN hub 212-232 does not receive several consecutive CPCM messages 272 during a time period cpcmTimeWindow, the MBAN hub 212-232 is triggered to switch its communication back to the ISM band. However, the lack of received CPCMs 272 may be a false positive rather than an actual indicator to stop using the MBAN spectrum. To prevent these false positive alarms on the MBAN hub 212-232, the hub 212-232 can periodically send information about received CPCMs 272 back to the control point 262. This message, called a Control Point Feedback Message (CPFM) 274, is shown in the example of FIG. 2. In general, the CPCM 272 and CPFM 274 traffic should be kept low to reduce energy consumption of the battery-operated MBAN hub devices 212-232. Based on these statistics the Control Point may analytically adjust the CPCMperiod for all devices or for a particular device that experiences a high number of false positive alarms over some predetermined period of time. Furthermore, the CPCMperiod may be adjusted by the P/C device analytically to increase of chance for an MBAN 210-230 to receive at least one CPCM message during cpcmTimeWindow. In this way, the MBAN 210-230 experiences fewer unnecessary transitions between the MBAN and ISM frequency band, which often translates to less disturbed MBAN networks and less data packet losses.

Figure 4A:
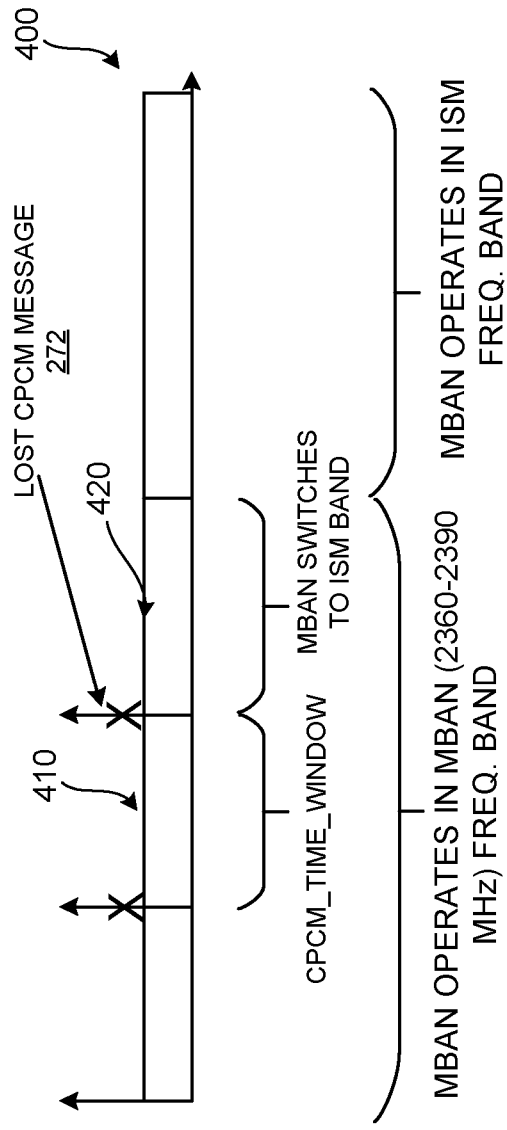
FIGS. 4A-4B show example timing diagrams for control message receipt and frequency band operation.
Figure 4B:
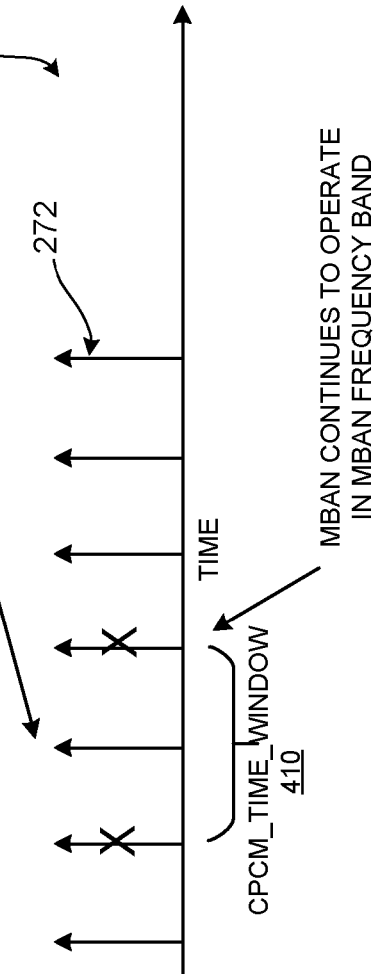

FIG. 4A illustrates an example 400 in which no CPCMs 272 transmitted by the control point 262 are received by the hub 212-232 during a time period cpcmTimeWindow 410. The MBAN hub 212-232 can then trigger a process to switch its communication back to the ISM frequency band in a time period 420. To prevent an unnecessary switch back to only ISM, rather than ISM+MBAN frequencies, a frequency of sending the CPCMs 272 can be increased as shown in example 450 of FIG. 4B. The increase in frequency of CPCM 272 transmission by the control point 262 helps to eliminate a possibility of unnecessary transitions of the MBAN hub 212-232 back to the ISM spectrum due no receipt any CPCM message 272 during the cpcmTimeWindow period 410. The adjustment of the CPCM period (e.g., to shorten the period and increase CPCM 272 frequency, etc.) helps to ensure that the MBAN hub 212-232 receives the CPCM 272 with higher reliability within the time window 410, allowing the MBAN to continue to operate in the MBAN frequency band if the band is available.

The CPCM 272 can include information about the channels in the MBAN spectrum which are available for use by MBAN devices. For example, the MBAN frequency coordinator 264 can allow only a subset of all MBAN channels in the 2360-2390 MHz band to be used by MBAN devices 210-230 in a hospital. In such an example, the CPCM 272 can carry information about available channels in the MBAN spectrum in an mbanAvailableChannelsBitmap field, for example.

A hospital and/or other healthcare environment may require that one or more MBAN devices 214-236 operate exclusively in the MBAN frequency spectrum when the MBAN spectrum becomes available. In such examples, the devices 214-236 can switch operations from ISM+MBAN frequencies to continue operating on the MBAN frequencies only. This information can be carried in an mbanOnly CPCM message field, for example.

Systems and methods enable frequency band switching for medical devices operating in medical body area networks (MBANs) in a healthcare environment. The devices operate in the ISM band, the MBAN band, or the expanded ISM plus MBAN frequency spectrum depending on operating condition, instruction, and/or coordinator 264 constraint, for example.

Depending upon a selected and/or otherwise designated frequency band of operation, an operating frequency and channel are determined for MBAN device communication. A single frequency or multiple frequencies can be selected, such as a channel that can be selected and designated as a default channel when the MBAN hub 212-232 needs to switch back to only the ISM band, for example.

In an example single frequency communication protocol, wireless devices that are within interference range of each other may suffer from excessive packet collisions and packet losses. One method to avoid operating on channel(s) at which the network experiences high packet losses is to change, periodically and/or adaptively, an operating frequency, for example. In case of adaptive frequency hopping, the network communicates using the same channel as long as a packet loss rate (or received signal strength indicator (RSSI), etc.) measured at the MBAN hub device 212-232 is below a packet loss threshold. When the MBAN hub device 212-232 starts experiencing high packet losses and/or a high level of interference, the hub 212-232 can trigger frequency hopping in which the network moves its communication to a new channel.

To determine a next channel, the MBAN hub device 212-232 can perform scanning of the channels in both the ISM and MBAN frequency bands when the hub 212-232 is not busy processing data and control packets. Channel scanning is an operation performed by a radio of the MBAN hub 212-232 during which signal power (expressed as a received signal strength indicator (RSSI)) at a certain frequency is measured. Channel scanning can be used to determine if the channel is actively used by other wireless devices or is within interference range of other wireless devices. If the channel is actively used by other wireless device(s) and/or is within an interference range of other wireless device(s), then that channel may not be a best candidate for use by a scanning MBAN hub 212-232, for example.

When the MBAN 210-230 is operating in the MBAN spectrum, the hub device 212-232 can scan ISM channels periodically, as triggered, and/or on demand, etc., to determine a "default ISM channel". The default ISM channel can be used by an MBAN 210-230 when the hub 212-232 is to return immediately to the ISM band. For example, when the received CPCM message 272 instructs the MBAN hub device 212-232 to switch its operation to the ISM band, or when a number of lost consecutive CPCMs 272 is higher than a predetermined threshold, the hub device 212-232 initiates switching to the default ISM channel.

In one example, the default ISM channel can be selected by keeping a list of X "best" channels, in which quality of a channel is determined by channel scanning (e.g., based on RSSI, etc.) and X<<N, where N is a total number of channels in the ISM band. The MBAN hub device 212-232 updates the best channel list every time the hub 212-232 scans the channel. The best ISM channel can then be determined as a channel randomly chosen among the best X channels in the list, for example.

Alternatively or in addition, a multi-frequency communication protocol can be applied to the MBAN hubs 212-232 to help ensure the hubs 212-232 receive CPCMs 272 published by the control point 262.

Figure 5:
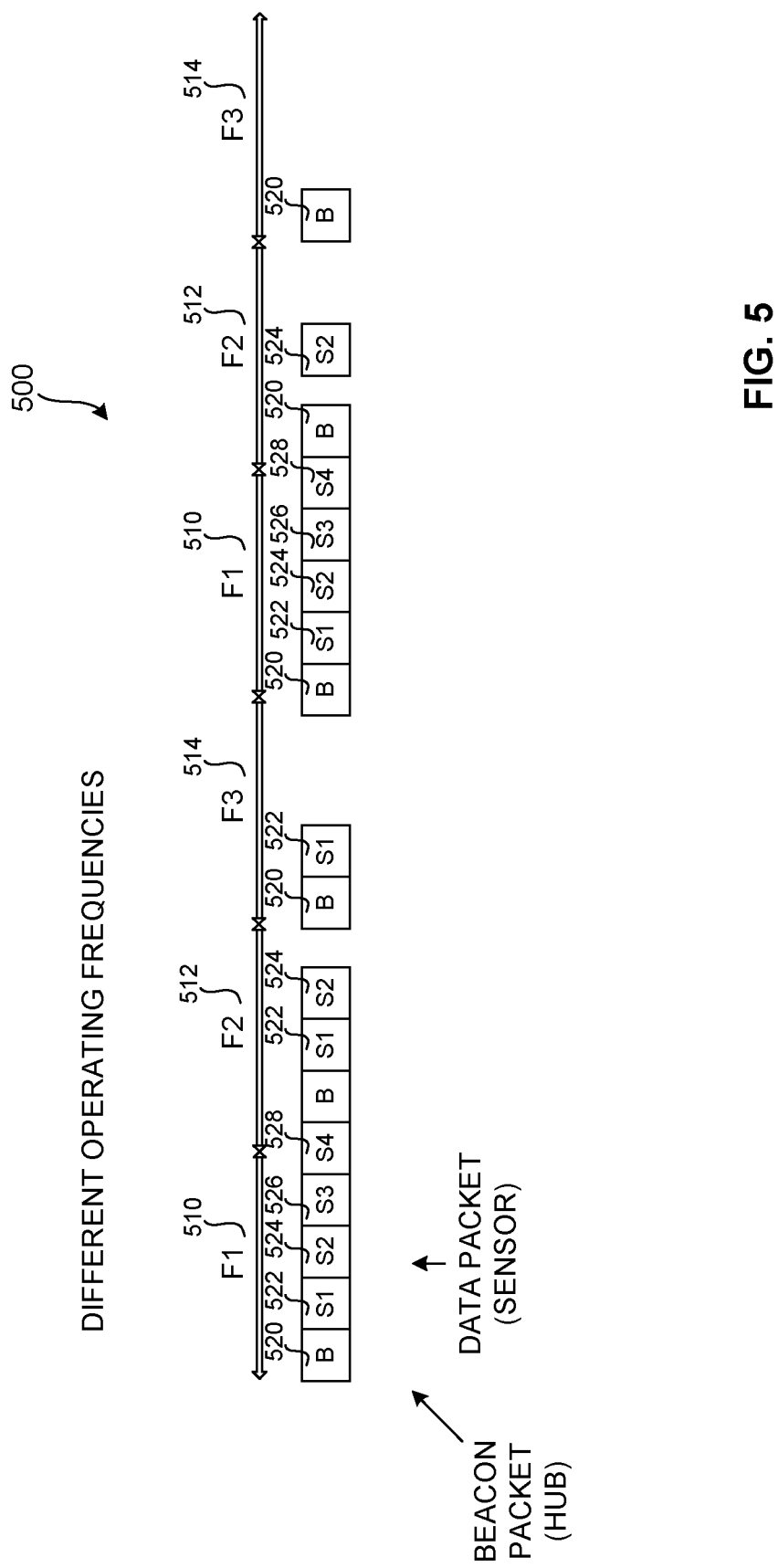
FIG. 5 shows an example multifrequency communication protocol.

In certain examples, a probability of successful packet reception by the MBAN hub 212-232 can be increased by retransmitting data packets. For example, MBAN devices can use a multifrequency communication protocol in which, to increase the probability of successful packet reception, the MBAN sensors 214-236 retransmit data packets on different frequencies. For example, time division multiple access (TDMA) can be used to transmit data packets from sensors 214-236 one after another to help assure no collisions between the packets within the same network. FIG. 5 shows one such multifrequency communication protocol 500, in which communication is organized in frames 510-514. During one frame 510, the sensors 214-236 transmit their packets 522-528 to the corresponding MBAN hub device 212-232. The MBAN hub 212-232 sends a beacon message 520 back to the sensors 214-236 at the beginning of each frame 510-514. The beacon message 520 is used for time synchronization between the hub 212-232 and sensors 214-236, and the beacon message 520 carries information regarding whether particular sensor(s) 214-236 are to retransmit their packets 522-528 in the new frame 510-514. The beacon message 520 also carries information about the next channel for each frame 510-514.

Having a protocol that can operate in both MBAN and ISM frequency bands provides significant advantages. For example, since the MBAN frequency spectrum is mostly free of high interfering devices, such as WiFi devices, data transmission in this frequency band increases a chance of successful data transmission. However, being able to keep part of communication in the ISM band provides a way to continue uninterrupted data transmission between sensor(s) 214-236 and a hub device 212-232 when there is a need for immediate frequency switching from the MBAN spectrum to the ISM spectrum, for example.

For example, if the MBAN spectrum is available for use, communication during F1 510 and F2 512 frames can be carried using available channels in the MBAN spectrum, while communication during F3 514 can be carried out using ISM channels only. The operating frequencies F1 510 and/or F2 512 may change periodically or adaptively (e.g., as described above). In certain examples, the F3 514 frequency, which operates in the ISM band, has less freedom in changing its value so that all devices in the network always know the current F3 514 value. For example, F3 514 can change periodically (e.g., according to a frequency pattern) or F3 514 can stay constant. When an MBAN 210-230 needs to switch from the MBAN spectrum to the ISM spectrum, the MBAN hub 212-232 is to move communication on F1 510 or/and F2 512 back to the ISM spectrum. For example, the hub device 212-232 can send a frequency switching command in its beacon messages 520 at the beginning of every frame 510-514. An MBAN network can start switching communication during F1 510 and/or F2 512 frame to the ISM spectrum gradually while still being able to retransmit the data packets on F3 514, if necessary, when the new selected channel(s) in the ISM band are already used by other MBAN devices.

Thus, certain examples provide an infrastructure and associated apparatus to enable MBANs 210-230 and their hubs 212-232 to operate on available frequency spectrum(-a) based on availability, operating conditions, control constraints, etc.

Figure 6:
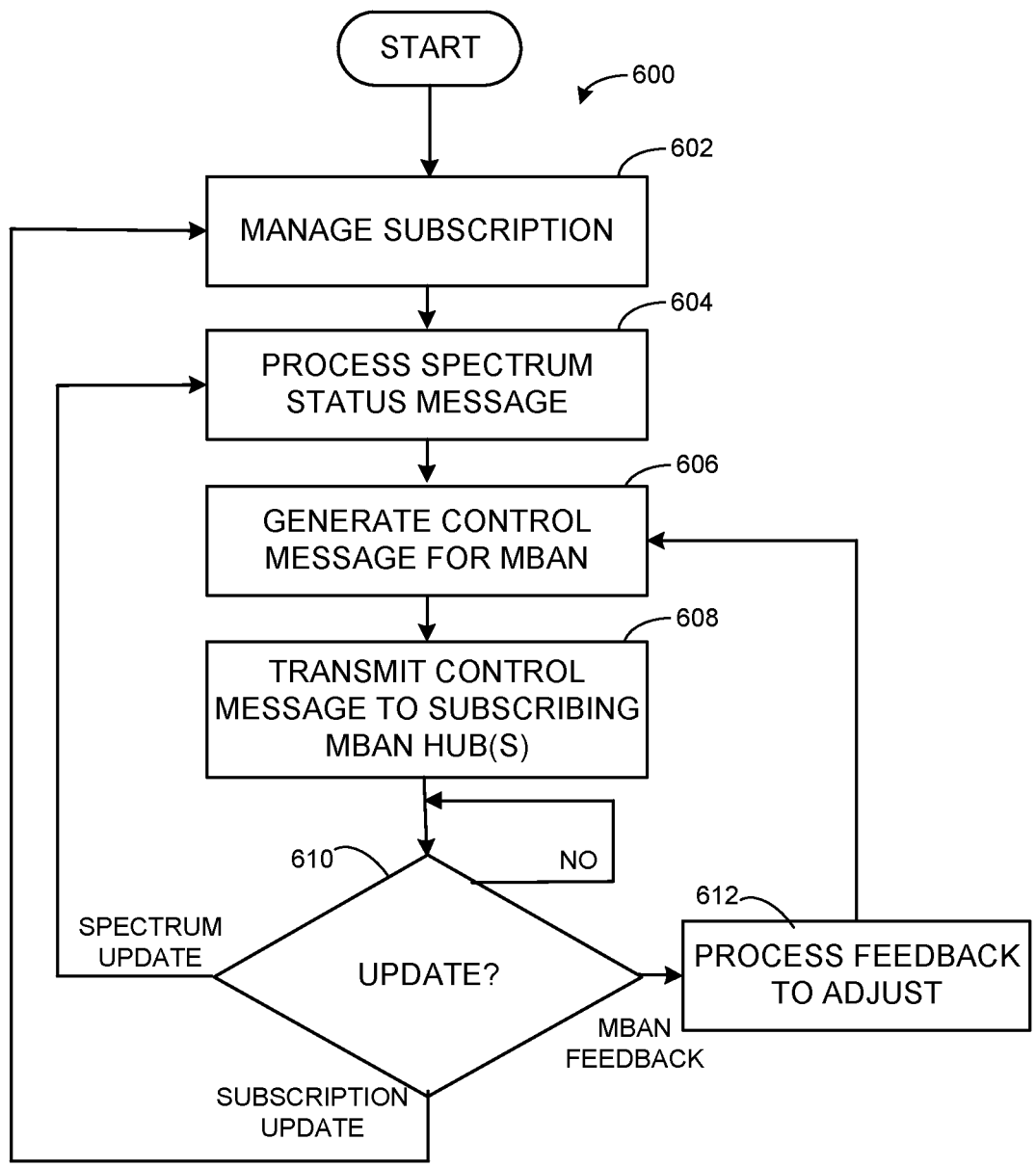
FIGS. 6-8 illustrate flow diagrams of example methods to control frequency band operation of an MBAN.

FIG. 6 illustrates an example method of distributing information to MBAN hubs 212-232 for frequency switching of MBANs 210-230. For example, the frequency coordinator 264, the central hospital coordinator 260, and/or its control point 262 can instruct and/or otherwise communicate with MBAN hub(s) 212-232 to configure and/or otherwise inform the hub(s) 212-232 (e.g., hub(s) 212-232 subscribing to a communication frequency topic, to the control point 262, etc.) regarding available and/or otherwise allocated frequency spectrum(-a) for MBAN communication.

At block 602, a subscription of one or more MBAN hubs 212-232 is managed at the control point 262. One or more MBAN hubs 212-232 can subscribe to one or more topics including a control point topic, for example. The control point topic is associated with a control point control message 272 specifying availability of a frequency spectrum for MBAN 210-230 usage.

At block 604, the control point 262 processes an MBAN spectrum status message 270 from the MBAN frequency coordinator 264. For example, the frequency coordinator 264 informs the control point 262, directly or via the central hospital coordinator 206, regarding availability of the MBAN spectrum versus the ISM spectrum. Thus, the MBAN spectrum status message 270 directly or indirectly tells the control point 262 which frequency spectrum is available for MBAN use.

At block 606, a CPCM 272 is generated by the control point 262 based on the information in the MBAN spectrum status message 270. For example, the control point 262 generates a CPCM 272 that includes a parameter indicating a frequency range available for use (e.g., 2360-2390 MHz, 2360-2400 MHz, etc.), a binary value triggering a configuration or other reaction by the MBAN hub 212-232 to operate in the MBAN spectrum or the ISM spectrum, and/or other value to configure the hub 212-232 in MBAN and/or ISM spectrum communication mode.

At block 608, the CPCM 272 is transmitted by the control point 262 to subscribing MBAN hub(s) 212-232. The example CPCM 272 includes information regarding available frequency spectrum (e.g., ISM and/or MBAN, etc.) and/or other command, instruction, or control parameter to configure operation of subscribing MBAN hub(s) 212-232 and their associated MBAN(s) 210-230.

At block 610, the control point 262 awaits feedback and/or other update. For example, the control point 262 awaits feedback from one or more MBAN hub devices 212-232 indicating whether or not the hub 212-232 has been receiving CPCMs 272, has not receive a CPCM 272 for a period of time, has missed a certain number of CPCMs 272, etc. The hub 212-232 can tell the control point 262 which frequency band (e.g., MBAN, ISM, ISM+MBAN, etc.) is being used for MBAN communication, etc.

If the update is feedback from an MBAN hub 212-232, then control proceeds to block 612 to process the feedback to adjust settings and/or other operation of the control point 262, for example. For example, the control point 262 can adjust a frequency of CPCM 272 transmission based on missed CPCM 272 and/or other feedback from the hub device(s) 212-232. The control point 262 can manage subscription based on the hub device(s) 212-232 feedback, for example, to help ensure that the proper hub device(s) 212-232 are receiving the appropriate messages to operate more efficiently and effectively in the available frequency spectra. Control then returns to block 606 to generate an updated CPCM 272.

Additionally, the frequency coordinator 264 can provide a new spectrum status message 270 to the control point 262, for example. When the spectrum status message 270 is received, control reverts to block 604 to process the spectrum status message 270.

Further, a subscription can be updated at the control point 262. For example, an MBAN hub 212-232 can subscribe to CPCM updates, unsubscribe, adjust frequency of CPCM 272 delivery, etc. When the subscription update is received, control reverts to block 602 to manage subscriptions of the control point 262.

Thus, the control point 262 of the example hospital system 200 can control and/or otherwise influence behavior of MBAN devices through their MBAN hubs 212-232 using CPCMs 272 to provide instructions and/or indications of frequency availability, operating constraints, modes, messaging frequency/sequence, other configuration information, etc.

Figure 7:
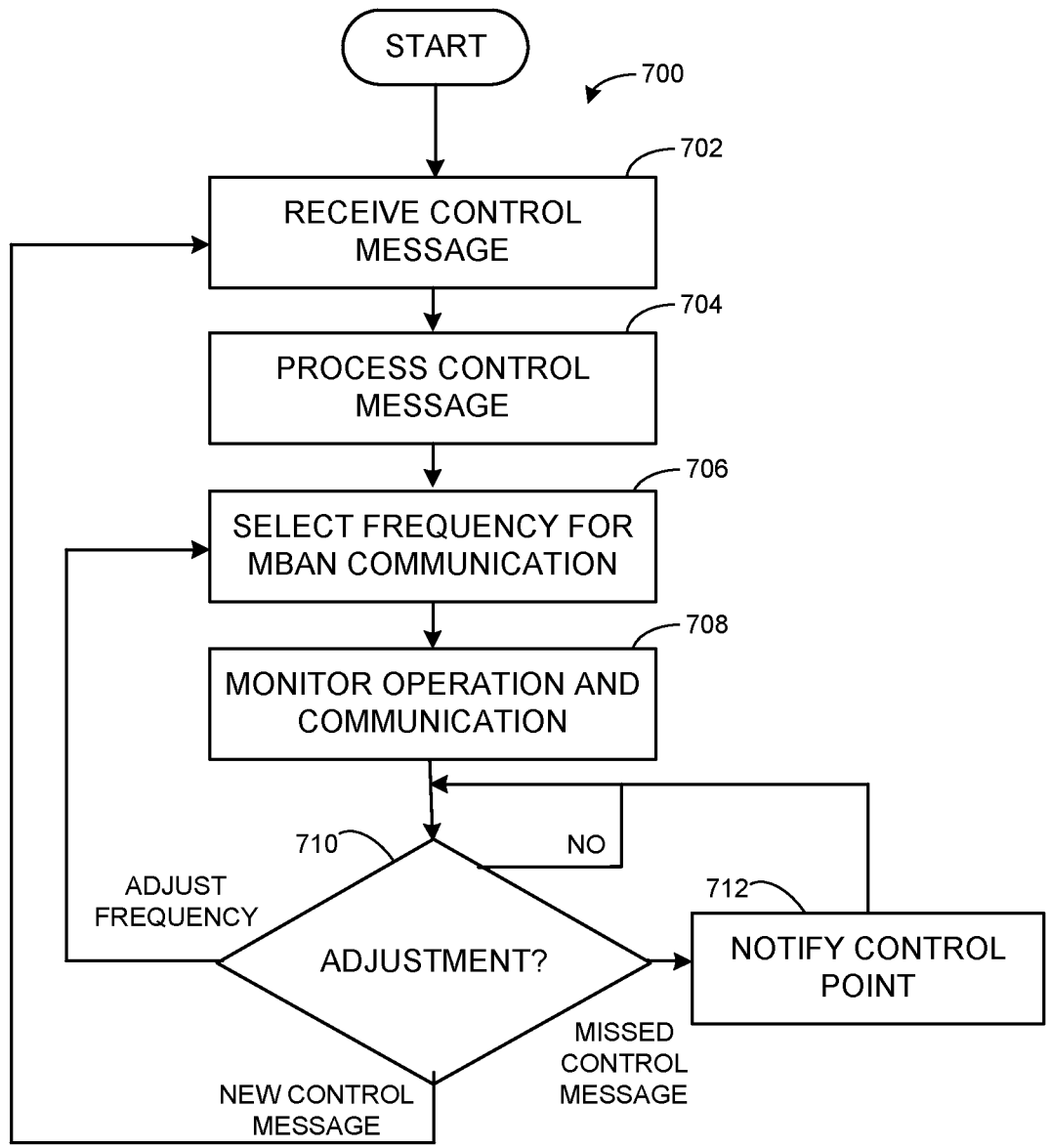

FIG. 7 illustrates an example method of configuration MBAN communication via the MBAN hubs 212-232. For example, MBAN hub(s) 212-232 configure, based on received messaging, available, preferred, and/or default communication frequency(-ies) for their associated MBAN devices 214-236 within the MBAN(s) 210-230.

At block 702, a CPCM 272 is received by an MBAN hub device 212-232. The CPCM 272 can be sent by the control point 262, for example, and include information, setting, and/or instruction regarding mode, available frequency, constraint, subscription, etc.

At block 704, the MBAN hub device 212-232 processes the CPCM 272 to determine which frequency(-ies) are available for MBAN communication. Determination can include available/permissible use of the ISM band, ISM band plus MBAN band, MBAN band, etc.

At block 706, the MBAN hub 212-232 selects one or more frequencies for communication with its MBAN 210-230 and associated devices 214-236. For example, the hub 212-232 can select a single ISM frequency, multiple frequencies including MBAN and ISM, a single MBAN frequency, etc.

At block 708, the MBAN hub 212-232 monitors its operation and communication. For example, the MBAN hub 212-232 evaluates whether it expected but did not receive a CPCM 272, has received a new CPCM 272, has experienced communication difficulties to switch to a new frequency channel, etc.

If a new CPCM 272 is received, then control reverts to block 702 to receive and process the new control message. If one or more (e.g., a certain number or threshold, etc.) of CPCMs 272 has not been received in a certain time window or period, then control moves to block 712 to notify the control point 262 of the missing CPCM(s) 272. If a communication frequency/channel is to be adjusted due to environmental conditions, location, outside instruction, loss/interference, etc., then control reverts to block 706 to select frequency(-ies) for communication in the MBAN 210-230. Thus, a single ISM frequency, multiple MBAN/ISM frequencies, etc., can be selected for communication in the MBAN 210-230, for example.

Figure 8:
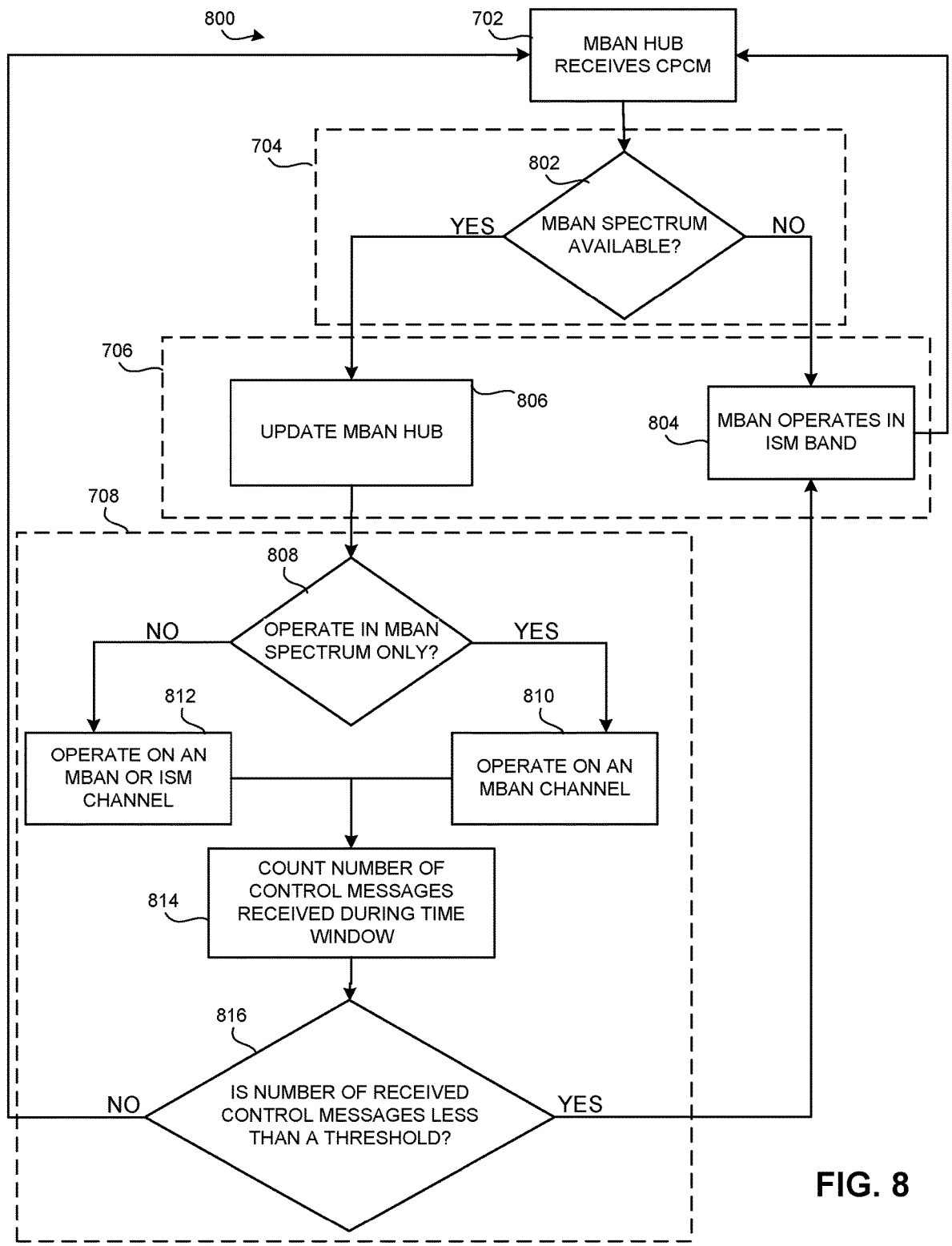

FIG. 8 illustrates a particular implementation 800 of the example method 700. As shown in the example method 800 of FIG. 8, at block 702, the MBAN hub 212-232 receives the CPCM 272. At block 802, an example implementation of block 704 of the example method 700, the CPCM 272 is analyzed by the hub 212-232 to determine whether the MBAN spectrum is available (versus only the ISM spectrum, etc.). If the MBAN spectrum is not available, then, at block 804, the MBAN hub 212-232 configures its MBAN 210-230 to communicate in the ISM band (e.g., at a particular or default ISM channel, etc.). The MBAN hub 212-232 facilitates communication in the ISM band until a new CPCM 272 is received at block 702, for example.

If the MBAN spectrum is available, then, at block 806, the MBAN hub 212-232 updates its settings/configuration based on the CPCM 272. For example, the MBAN hub 212-232 can set a period for a frequency of or how often to expect CPCM 272 receipt by the hub 212-232 (CPCM_PERIOD), a time window during which the CPCM 272 is to be received (CPCM_TIME_WINDOW), a maximum number of missed messages to trigger a notification to the control point 262 (CPCM_MAX_MISSED_MSGS), an indication or listing of available channels (MBAN_AVAILABLE_CHANNELS), etc.

At block 708, the MBAN hub 212-232 then monitors its operation and communication. For example, at block 808, the MBAN hub device 212-232 configuration is checked to determine whether the MBAN 210-230 is to operate in the MBAN spectrum only. If the MBAN 210-230 is to operate in the MBAN frequency spectrum only, then, at block 810, an MBAN channel is selected by the hub 212-232 for communication in that MBAN 210-230. If the MBAN 210-230 is to operate in the MBAN and ISM frequency spectra, then, at block 812, an MBAN channel or an ISM channel is selected by the hub 212-232 for communication in the respective MBAN 210-230.

At block 814, the MBAN hub device 212-232 counts or otherwise tracks a number of CPCMs 272 received in a time window. For example, the hub 212-232 configuration specifies a time period or window during which a certain number of CPCMs 272 are to be received. The hub 212-232 keeps track of received CPCM(s) 272 during that time window.

At block 816, the number of received CPCM(s) 272 in the time period is compared to a threshold or other criterion to determine whether the threshold/criterion is satisfied by the number of received CPCM(s) 272 during the time window. For example, the hub 212-232 configuration can specify an expected number of messages for the time window. If the number of received CPCM(s) 272 is less than the number of expected CPCM(s) 272 and/or a minimum viable/allowable threshold of CPCM(s) 272, then the threshold/criterion is not met/satisfied. If the number of received CPCM(s) 272 is greater than or equal to or otherwise does not satisfy the threshold/criterion, then the MBAN hub 212-232 switches to block 804 to operate its MBAN 210-230 in the ISM band only. If the number of received CPCM(s) 272 is less than or otherwise satisfies the threshold/criterion, then the MBAN hub 212-232 switches to block 702 to await receipt of a CPCM 272 from the control point 262.

Thus, certain examples provide improved, automated, dynamic frequency switching for MBAN operation in and out of a healthcare facility. Certain examples provide technologically improved operation to help maximize or otherwise improve usage of available bandwidth for MBAN devices while also reducing or minimizing conflicts with other medical devices using overlapping frequency(-ies) range(s). Certain examples provide a technological benefit in medical device monitoring and communications by improving performance of a wireless ambulatory monitoring system by allowing for more intelligent and proactive frequency band selection and hopping.

One skilled in the art will appreciate that embodiments of the invention may be interfaced to and controlled by a computer readable storage medium having stored thereon a computer program. The computer readable storage medium includes a plurality of components such as one or more of electronic components, hardware components, and/or computer software components. These components may include one or more computer readable storage media that generally stores instructions such as software, firmware and/or assembly language for performing one or more portions of one or more implementations or embodiments of a sequence. These computer readable storage media are generally non-transitory and/or tangible. Examples of such a computer readable storage medium include a recordable data storage medium of a computer and/or storage device. The computer readable storage media may employ, for example, one or more of a magnetic, electrical, optical, biological, and/or atomic data storage medium. Further, such media may take the form of, for example, floppy disks, magnetic tapes, CD-ROMs, DVD-ROMs, hard disk drives, and/or electronic memory. Other forms of non-transitory and/or tangible computer readable storage media not list may be employed with embodiments of the invention.

A number of such components can be combined or divided in an implementation of a system. Further, such components may include a set and/or series of computer instructions written in or implemented with any of a number of programming languages, as will be appreciated by those skilled in the art. In addition, other forms of computer readable media such as a carrier wave may be employed to embody a computer data signal representing a sequence of instructions that when executed by one or more computers causes the one or more computers to perform one or more portions of one or more implementations or embodiments of a sequence.

Figure 9:
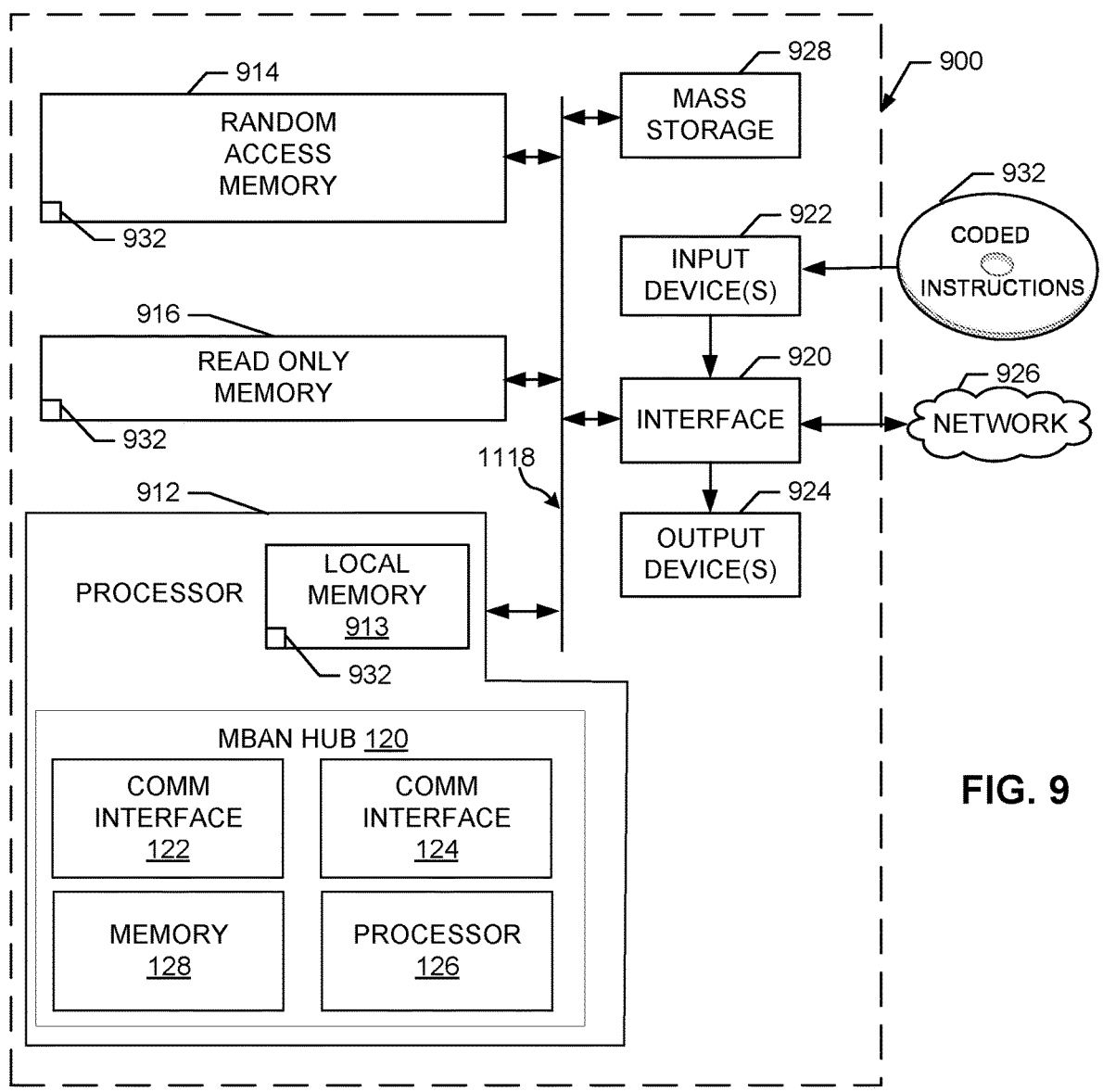
FIGS. 9-10 are block diagrams of an example processor platforms that can execute instructions to implement the example systems and methods of FIGS. 1-8.

FIG. 9 is a block diagram of an example processor platform 900 that can execute instructions to implement the example systems and methods of FIGS. 1-8. The processor platform 900 can be, for example, a server, a personal computer, a mobile device (e.g., a cell phone, a smart phone, a tablet such as an IPAD™), a personal digital assistant (PDA), an Internet appliance, or any other type of computing device.

The processor platform 900 of the illustrated example includes a processor 912. Processor 912 of the illustrated example is hardware. For example, processor 912 can be implemented by one or more integrated circuits, logic circuits, microprocessors or controllers from any desired family or manufacturer.

Processor 912 of the illustrated example includes a local memory 913 (e.g., a cache). Processor 912 of the illustrated example is in communication with a main memory including a volatile memory 914 and a non-volatile memory 916 via a bus 918. Volatile memory 914 can be implemented by Synchronous Dynamic Random Access Memory (SDRAM), Dynamic Random Access Memory (DRAM), RAMBUS Dynamic Random Access Memory (RDRAM) and/or any other type of random access memory device. The non-volatile memory 916 can be implemented by flash memory and/or any other desired type of memory device. Access to main memory 914, 916 is controlled by a memory controller. The processor 912, alone or in conjunction with the memory 913, can be used to implement the MBAN hub 212 including its communication interfaces 122, 124, processor 126, memory 128, and/or other part of the systems disclosed herein.

Processor platform 900 of the illustrated example also includes an interface circuit 920. Interface circuit 920 can be implemented by any type of interface standard, such as an Ethernet interface, a universal serial bus (USB), and/or a PCI express interface.

In the illustrated example, one or more input devices 922 are connected to the interface circuit 920. Input device(s) 922 permit(s) a user to enter data and commands into processor 912. The input device(s) 922 can be implemented by, for example, an audio sensor, a microphone, a camera (still or video), a keyboard, a button, a mouse, a touchscreen, a track-pad, a trackball, isopoint and/or a voice recognition system.

One or more output devices 924 are also connected to interface circuit 920 of the illustrated example. Output devices 924 can be implemented, for example, by display devices (e.g., a light emitting diode (LED), an organic light emitting diode (OLED), a liquid crystal display, a cathode ray tube display (CRT), a touchscreen, a tactile output device, a light emitting diode (LED), a printer and/or speakers). Interface circuit 920 of the illustrated example, thus, typically includes a graphics driver card, a graphics driver chip or a graphics driver processor.

Interface circuit 920 of the illustrated example also includes a communication device such as a transmitter, a receiver, a transceiver, a modem and/or network interface card to facilitate exchange of data with external machines (e.g., computing devices of any kind) via a network 926 (e.g., an Ethernet connection, a digital subscriber line (DSL), a telephone line, coaxial cable, a cellular telephone system, etc.).

Processor platform 900 of the illustrated example also includes one or more mass storage devices 928 for storing software and/or data. Examples of such mass storage devices 928 include floppy disk drives, hard drive disks, compact disk drives, Blu-ray disk drives, RAID systems, and digital versatile disk (DVD) drives.

Coded instructions 932 associated with any of FIGS. 1-8 can be stored in mass storage device 928, in volatile memory 914, in the non-volatile memory 916, and/or on a removable tangible computer readable storage medium such as a CD or DVD.

It may be noted that operations performed by the processor platform 900 (e.g., operations corresponding to process flows or methods discussed herein, or aspects thereof) may be sufficiently complex that the operations may not be performed by a human being within a reasonable time period.

Figure 10:
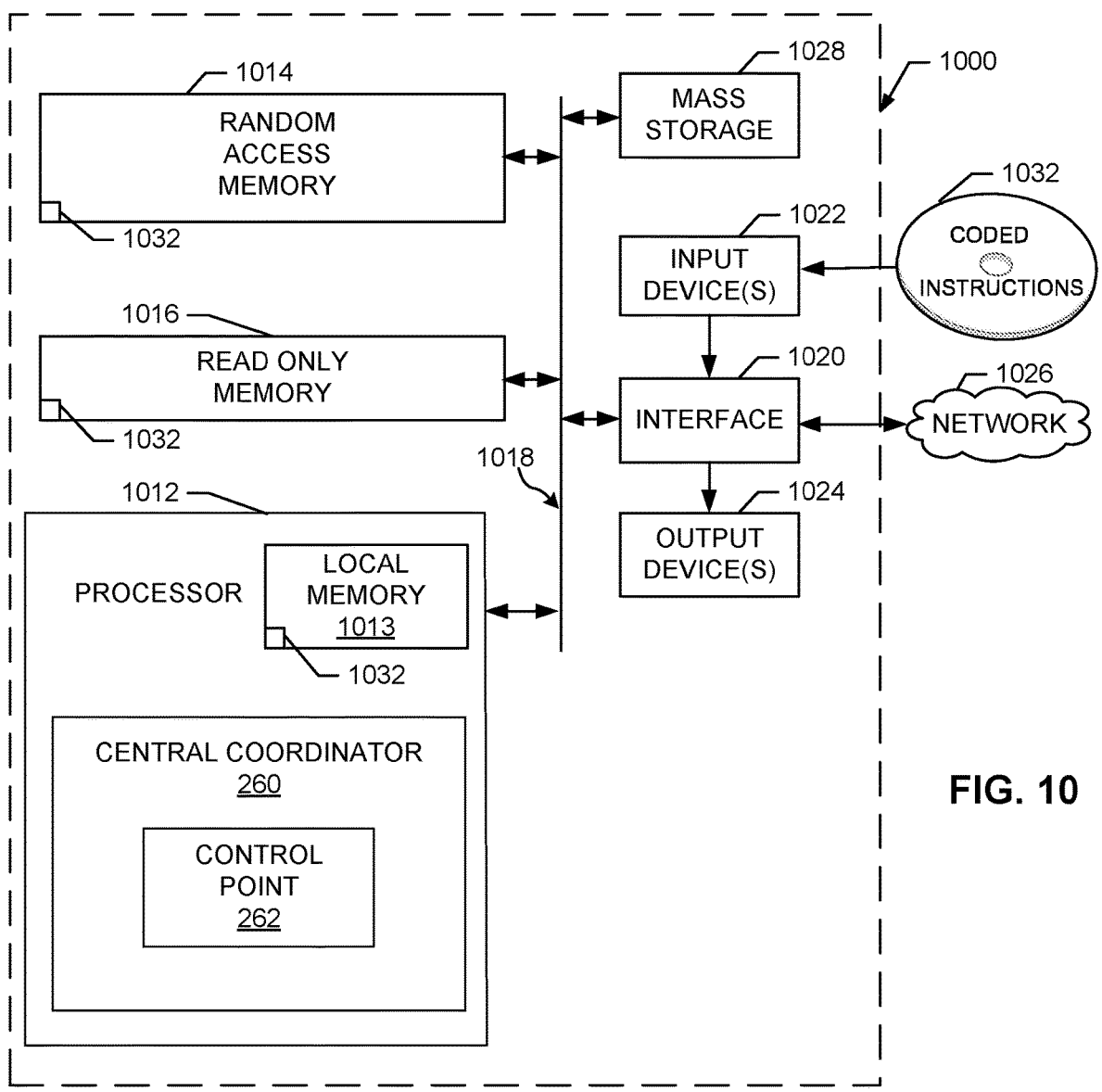

FIG. 10 is a block diagram of an example processor platform 1000 that can execute instructions to implement the example systems and methods of FIGS. 1-8. The processor platform 1000 can be, for example, a server, a personal computer, a mobile device (e.g., a cell phone, a smart phone, a tablet such as an IPAD™, a personal digital assistant (PDA), an Internet appliance, or any other type of computing device.

The processor platform 1000 of the illustrated example includes a processor 1012. Processor 1012 of the illustrated example is hardware. For example, processor 1012 can be implemented by one or more integrated circuits, logic circuits, microprocessors or controllers from any desired family or manufacturer.

Processor 1012 of the illustrated example includes a local memory 1013 (e.g., a cache). Processor 1012 of the illustrated example is in communication with a main memory including a volatile memory 1014 and a non-volatile memory 1016 via a bus 1018. Volatile memory 1014 can be implemented by Synchronous Dynamic Random Access Memory (SDRAM), Dynamic Random Access Memory (DRAM), RAMBUS Dynamic Random Access Memory (RDRAM) and/or any other type of random access memory device. The non-volatile memory 1016 can be implemented by flash memory and/or any other desired type of memory device. Access to main memory 1014, 1016 is controlled by a memory controller. The processor 1012, alone or in conjunction with the memory 1013, can be used to implement the central coordinator 260, control point 262, and/or other part of the systems disclosed herein.

Processor platform 1000 of the illustrated example also includes an interface circuit 1020. Interface circuit 1020 can be implemented by any type of interface standard, such as an Ethernet interface, a universal serial bus (USB), and/or a PCI express interface.

In the illustrated example, one or more input devices 1022 are connected to the interface circuit 1020. Input device(s) 1022 permit(s) a user to enter data and commands into processor 1012. The input device(s) 1022 can be implemented by, for example, an audio sensor, a microphone, a camera (still or video), a keyboard, a button, a mouse, a touchscreen, a track-pad, a trackball, isopoint and/or a voice recognition system.

One or more output devices 1024 are also connected to interface circuit 1020 of the illustrated example. Output devices 1024 can be implemented, for example, by display devices (e.g., a light emitting diode (LED), an organic light emitting diode (OLED), a liquid crystal display, a cathode ray tube display (CRT), a touchscreen, a tactile output device, a light emitting diode (LED), a printer and/or speakers). Interface circuit 1020 of the illustrated example, thus, typically includes a graphics driver card, a graphics driver chip or a graphics driver processor.

Interface circuit 1020 of the illustrated example also includes a communication device such as a transmitter, a receiver, a transceiver, a modem and/or network interface card to facilitate exchange of data with external machines (e.g., computing devices of any kind) via a network 1026 (e.g., an Ethernet connection, a digital subscriber line (DSL), a telephone line, coaxial cable, a cellular telephone system, etc.).

Processor platform 1000 of the illustrated example also includes one or more mass storage devices 1028 for storing software and/or data. Examples of such mass storage devices 1028 include floppy disk drives, hard drive disks, compact disk drives, Blu-ray disk drives, RAID systems, and digital versatile disk (DVD) drives.

Coded instructions 1032 associated with any of FIGS. 1-8 can be stored in mass storage device 1028, in volatile memory 1014, in the non-volatile memory 1016, and/or on a removable tangible computer readable storage medium such as a CD or DVD.

It may be noted that operations performed by the processor platform 1000 (e.g., operations corresponding to process flows or methods discussed herein, or aspects thereof) may be sufficiently complex that the operations may not be performed by a human being within a reasonable time period.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

Although certain example methods, apparatus and articles of manufacture have been disclosed herein, the scope of coverage of this patent is not limited thereto. On the contrary, this patent covers all methods, apparatus and articles of manufacture fairly falling within the scope of the claims of this patent.

What is claimed is:

1. An apparatus comprising:
    at least one processor to determine, based on a plurality of control messages indicating availability of a second frequency spectrum and timing of receipt of the plurality of control messages, a first mode or a second mode for medical body area network (MBAN) communication, the first mode specifying MBAN communication in a first frequency spectrum and the second mode specifying MBAN communication in the first frequency spectrum and the second frequency spectrum, wherein, when MBAN communication is in the second mode, the at least one processor is to:
    count a number of control messages received in a period of time;
    compare the number of received control messages to a threshold; and
    when the number of received control messages is less than the threshold, switch MBAN communication to the first mode; and
    at least one communication interface to receive the control messages from a controller and to transmit an indication of a missed control message to trigger an adjustment of control messages transmission in the period of time by the controller.

2. The apparatus of claim 1, wherein the apparatus is an MBAN hub device, and wherein the controller is a control point.

3. The apparatus of claim 2, wherein the MBAN hub device is a subscriber to receive the control messages from the control point.

4. The apparatus of claim 1, wherein the plurality of control messages further include a spectrum status message received from a frequency coordinator.

5. The apparatus of claim 1, wherein the indication is associated with an adjustment in a rate of transmission of control messages from the controller to an MBAN hub device.

6. The apparatus of claim 1, wherein a default channel for communication in the first frequency spectrum is to be determined by periodically scanning channels in the first frequency spectrum and stored.

7. At least one computer-readable storage medium including instructions that, when executed, cause at least one processor to at least:
    determine, based on a plurality of control messages indicating availability of a second frequency spectrum and timing of receipt of the plurality of control messages, a first mode or a second mode for medical body area network (MBAN) communication, the first mode specifying MBAN communication in a first frequency spectrum and the second mode specifying MBAN communication in the first frequency spectrum and the second frequency spectrum;

when MBAN communication is in the second mode:
count a number of control messages received in a period of time from a controller;
compare the number of received control messages to a threshold; and
when the number of received control messages is less than the threshold, switch MBAN communication to the first mode; and
transmit an indication of a missed control message to trigger an adjustment of control messages transmission in the period of time by the controller.

8. The storage medium of claim 7, wherein the at least one computer-readable storage medium is included in an MBAN hub device including the at least one processor, and wherein the controller is a control point.

9. The storage medium of claim 8, wherein the MBAN hub device is a subscriber to receive the control message from the control point.

10. The storage medium of claim 7, wherein the plurality of control messages further include a spectrum status message received from a frequency coordinator.

11. The storage medium of claim 7, wherein the indication is associated with an adjustment in a rate of transmission of control messages from the controller to an MBAN hub device.

12. The storage medium of claim 7, wherein the instructions, when executed, cause the at least one processor to determine a default channel for communication in the first frequency spectrum by periodically scanning channels in the first frequency spectrum and stored.

13. A method comprising:
determining, using at least one processor based on a plurality of control messages indicating availability of a second frequency spectrum and timing of receipt of the plurality of control messages, a first mode or a second mode for medical body area network (MBAN) communication, the first mode specifying MBAN communication in a first frequency spectrum and the second mode specifying MBAN communication in the first frequency spectrum and the second frequency spectrum;
when MBAN communication is in the second mode:
counting a number of control messages received in a period of time from a controller;
comparing the number of received control messages to a threshold; and
when the number of received control messages is less than the threshold, switching MBAN communication to the first mode; and
transmitting, using the at least one processor, an indication of a missed control message to trigger an adjustment of control messages transmission in the period of time by the controller.

14. The method of claim 13, wherein the at least one processor is included in an MBAN hub device, and wherein the the controller is a control point.

15. The method of claim 14, wherein the MBAN hub device is a subscriber to receive the control message from the control point.

16. The method of claim 13, wherein the plurality of control messages further include a spectrum status message received from a frequency coordinator.

17. The method of claim 13, wherein the indication is associated with an adjustment in a rate of transmission of control messages from the controller to an MBAN hub device.

* * * * *